United States Patent
Keller et al.

(10) Patent No.: US 10,398,406 B2
(45) Date of Patent: Sep. 3, 2019

(54) ONE PIECE STETHOSCOPE DIAPHRAGM

(71) Applicant: 3M INNOVATIVE PROPERTIES COMPANY, St. Paul, MN (US)

(72) Inventors: Joseph P. Keller, Wahpeton, ND (US); Dean Sitz, Wahpeton, ND (US); Mary Jo Johnson, Lake Elmo, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 111 days.

(21) Appl. No.: 15/500,128

(22) PCT Filed: Jul. 30, 2015

(86) PCT No.: PCT/US2015/042851
§ 371 (c)(1),
(2) Date: Jan. 30, 2017

(87) PCT Pub. No.: WO2016/022380
PCT Pub. Date: Feb. 11, 2016

(65) Prior Publication Data
US 2018/0214114 A1    Aug. 2, 2018

Related U.S. Application Data

(60) Provisional application No. 62/032,844, filed on Aug. 4, 2014.

(51) Int. Cl.
*A61B 7/02* (2006.01)
*A61B 7/00* (2006.01)
*G10K 11/18* (2006.01)

(52) U.S. Cl.
CPC .................. *A61B 7/02* (2013.01); *A61B 7/00* (2013.01); *G10K 11/18* (2013.01)

(58) Field of Classification Search
CPC .............. A61B 7/00; A61B 7/02; A61B 7/026
See application file for complete search history.

(56) References Cited

U.S. PATENT DOCUMENTS

| 4,200,169 A |   | 4/1980 | MacDonald, III |
|---|---|---|---|
| 4,440,258 A |   | 4/1984 | Packard |
| 4,461,368 A | * | 7/1984 | Plourde ................... A61B 7/02 181/131 |
| 4,770,270 A |   | 9/1988 | Grimm |
| 4,852,684 A |   | 8/1989 | Packard |

(Continued)

FOREIGN PATENT DOCUMENTS

| CN | 201409932 Y | 2/2010 |
|---|---|---|
| CN | 201409934 Y | 2/2010 |

(Continued)

OTHER PUBLICATIONS

International Search Report for PCT International Application No. PCT/US2015/042851, dated Feb. 11, 2016, 7 pages.

(Continued)

*Primary Examiner* — Edgardo San Martin
(74) *Attorney, Agent, or Firm* — 3M Innovative Properties Company; Jonathan V. Sry

(57) ABSTRACT

The present invention is a diaphragm including a disc formed from a first material and a rim formed from a second material. The disc and the rim are a unitary piece. The rim has a Shore A durometer hardness of between about 40 and 110.

13 Claims, 12 Drawing Sheets

(56) References Cited

U.S. PATENT DOCUMENTS

| | | | |
|---|---|---|---|
| 4,913,259 A | 4/1990 | Packard | |
| 4,995,473 A * | 2/1991 | Packard | A61B 7/02 181/131 |
| 5,111,904 A | 5/1992 | Packard | |
| 5,324,471 A | 6/1994 | Packard | |
| 5,380,182 A | 1/1995 | Packard | |
| 5,449,865 A | 9/1995 | Desnick | |
| 5,616,890 A * | 4/1997 | Boussignac | A61B 7/026 181/131 |
| 5,796,053 A * | 8/1998 | Shieh | A61B 7/02 181/131 |
| 5,910,992 A * | 6/1999 | Ho | A61B 7/026 181/131 |
| 5,931,792 A * | 8/1999 | Packard | A61B 7/026 181/131 |
| 5,932,849 A * | 8/1999 | Dieken | A61B 7/04 181/131 |
| 5,945,640 A | 8/1999 | Rossini | |
| 6,019,187 A * | 2/2000 | Appavu | A61B 7/02 181/131 |
| 6,244,376 B1 * | 6/2001 | Granzotto | A61B 7/02 181/131 |
| 6,378,648 B1 | 4/2002 | Werblud | |
| 6,523,639 B1 | 2/2003 | Shieh | |
| 7,424,929 B1 | 9/2008 | Martinez | |
| 7,757,807 B1 | 7/2010 | Martinez | |
| 9,770,307 B2 * | 9/2017 | Krupnick | A61B 7/02 |
| 2008/0093157 A1 | 4/2008 | Drummond | |

FOREIGN PATENT DOCUMENTS

| | | | |
|---|---|---|---|
| CN | 103156635 A | 6/2013 | |
| CN | 203710039 | 7/2014 | |
| DE | 212013000288 U1 * | 11/2015 | A61B 7/02 |

OTHER PUBLICATIONS

China National Intellectual Property Administration Search Report for CN201580042042.4.

* cited by examiner

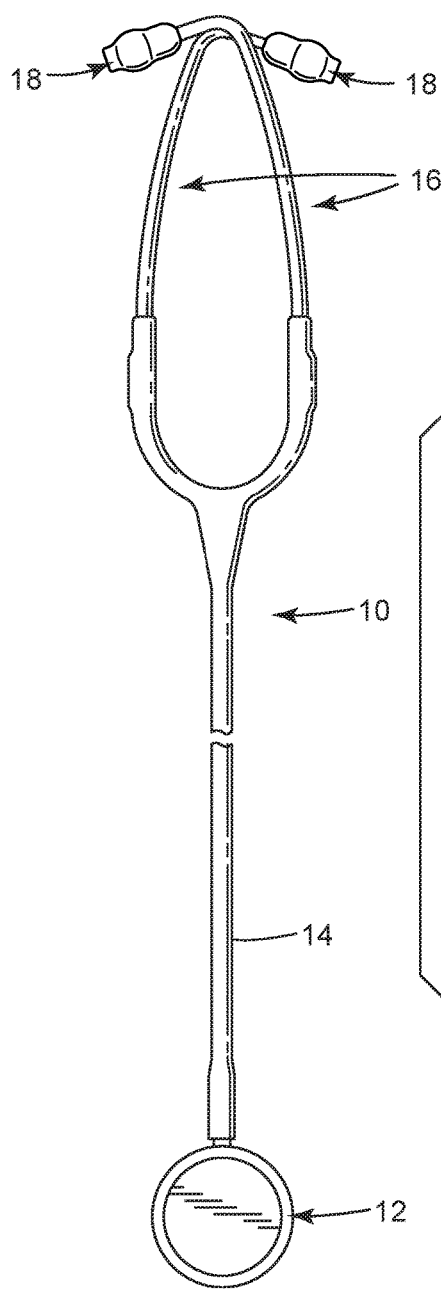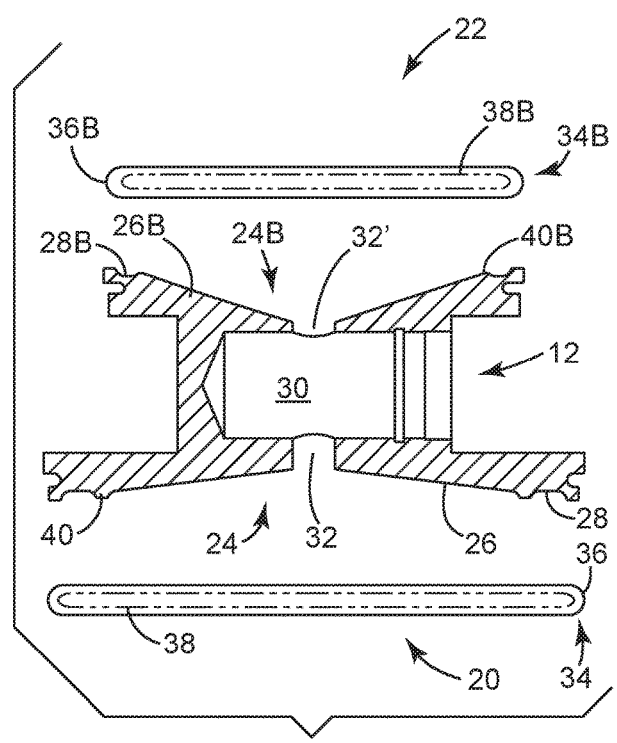
FIG. 1
FIG. 2

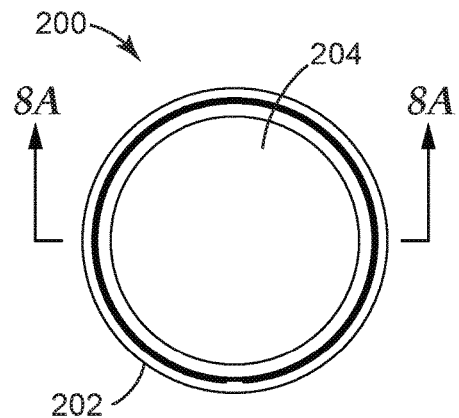
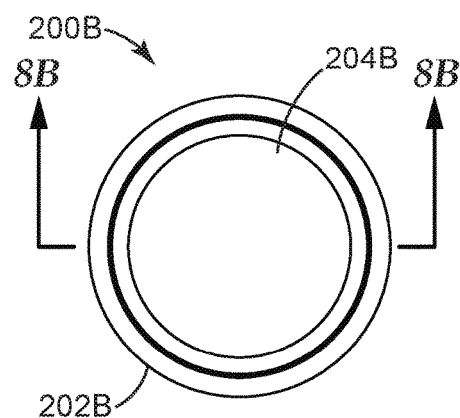
*FIG. 7A*  *FIG. 7B*
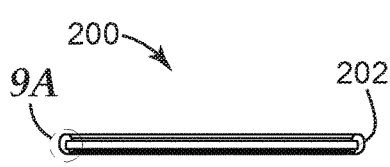
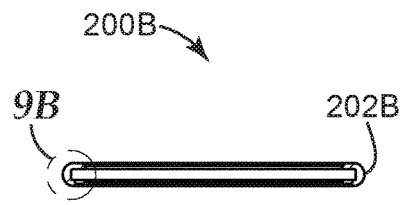
*FIG. 8A*  *FIG. 8B*
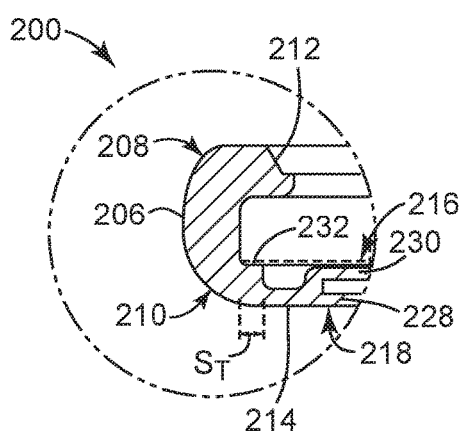
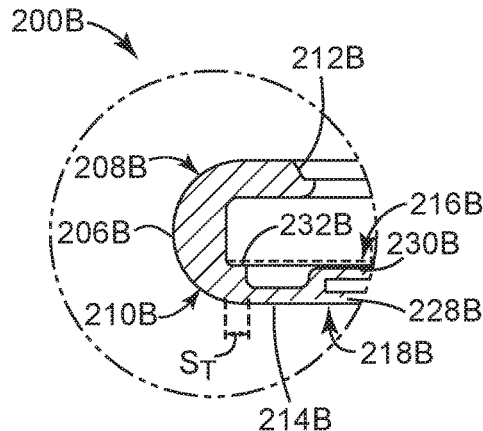
*FIG. 9A*  *FIG. 9B*

ONE PIECE STETHOSCOPE DIAPHRAGM

CROSS REFERENCE TO RELATED APPLICATIONS

This application is a national stage filing under 35 U.S.C. 371 of PCT/US2015/042851, filed Jul. 30, 2015, which claims the benefit of U.S. Provisional Application No. 62/032,844, filed Aug. 4, 2014, the disclosure of which is incorporated by reference in its/their entirety herein.

FIELD OF THE INVENTION

The present invention relates to stethoscopes. More particularly, it relates to one piece diaphragms that can be positioned on a chestpiece of a stethoscope.

BACKGROUND

Complete diagnosis of a patient using a stethoscope often requires that a physician monitor low frequency and high frequency sounds associated with, for example, the heart. With respect to the heart, it is important that the physician alternate between the monitoring of low frequency and high frequency sounds so that the physician does not lose the impression from the previously heard heartbeat before the next beat is heard. Without the benefit of tunable technology, the clinician would be required to turn the chestpiece over to hear additional sounds.

The diaphragms currently used on most stethoscopes are made of two pieces, the diaphragm and the rim. The rim is used to hold the diaphragm on the chestpiece. While this construction works very well to hold the components on the chestpiece, the process for manufacturing the two piece rim/diaphragm construction requires numerous operators to produce the assembled rim/diaphragm constructions. Generally, operators are needed to manually mold the diaphragms, to manually mold the rims, to manually trim runners from diaphragms, to manually assemble the diaphragms into the rims, and to inspect all assembled products.

SUMMARY

In one embodiment, the present invention is a diaphragm including a disc formed from a first material and a rim formed from a second material. The disc and the rim are a unitary piece. The rim has a Shore A durometer hardness of between about 40 and 110.

In another embodiment, the present invention is a stethoscope including a chestpiece and a first one piece diaphragm positionable on the chestpiece. The one piece diaphragm includes a disc made of a first material and a rim made of a second material. The rim has a Shore A durometer hardness of between about 40 and 110.

In yet another embodiment, the present invention is a method of making a one piece diaphragm. The method includes providing an injection mold, providing a circular disc formed from a first material, positioning the disc within the injection mold, providing a second material, heating the second material, melt molding the second material into the injection mold and around a peripheral edge of the disc to form a one piece diaphragm, and removing the one piece diaphragm from the injection mold.

BRIEF DESCRIPTION OF THE DRAWINGS

These figures are not drawn to scale and are intended merely for illustrative purposes.

FIG. 1 is a schematic view of a stethoscope using one piece diaphragms according to the present invention.

FIG. 2 is an enlarged, exploded, partial sectional view of a chestpiece of the stethoscope of FIG. 1.

FIG. 7A is a top view of a second embodiment of an adult-sized one piece diaphragm of the present invention.

FIG. 7B is a top view of a second embodiment of a pediatric-sized one piece diaphragm of the present invention.

FIG. 8A is a cross-sectional view of the second embodiment of an adult-sized one piece diaphragm of the present invention along lines 8A-8A of FIG. 7A.

FIG. 8B is a cross-sectional view of the second embodiment of a pediatric-sized one piece diaphragm of the present invention along lines 8B-8B of FIG. 7B.

FIG. 9A is an enlarged view of a part of the second embodiment of the adult-sized one piece diagram of the present invention shown in FIGS. 7A and 8A.

FIG. 9B is an enlarged view of a part of the second embodiment of the pediatric-sized one piece diagram of the present invention shown in FIGS. 7B and 8B.

DETAILED DESCRIPTION

Figure 3A:
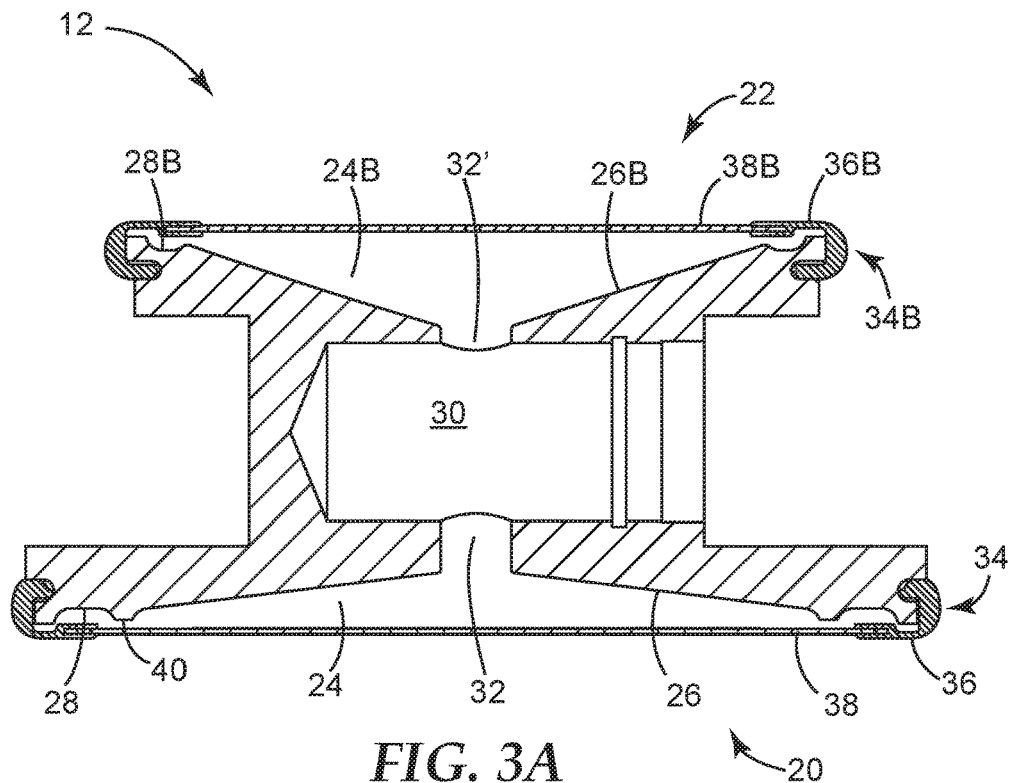
FIG. 3A is a cross-sectional view of an assembled chestpiece showing the one piece diaphragms of the present invention in an outer position.

The present invention is a one piece diaphragm to be used with stethoscopes. In one embodiment, the stethoscopes are tunable stethoscopes. An advantage of the one piece diaphragm is the ability to easily and thoroughly clean the diaphragm. Due to the elimination of the gap between the diaphragm and the rim that is present in current two piece designs, the one piece diaphragm eliminates locations for bacteria to grow. This is particularly true on the surface of the diaphragm that contacts the patient. The one piece diaphragm of the present invention allows the entire surface to be cleaned. In current two piece designs, the disc and rim must be disassembled in order to be thoroughly cleaned, which can be difficult and time-consuming. In addition, the one piece diaphragm is also significantly easier for the user to install than conventional two-piece diaphragms. Furthermore, the one piece diaphragm of the present invention can be easily produced at low cost. This can allow for manufacturing disposable diaphragms for treating patients with contagious diseases or easily producing custom made diaphragms.

As used in the instant specification and claims, "acoustical stiffness" of the diaphragm designates the mechanical stiffness of the diaphragm as influenced by the mechanical stiffness of the diaphragm material itself, the thickness of the diaphragm, the shape of the diaphragm, the diameter of the diaphragm, and the manner in which the diaphragm is attached to the stethoscope head. The phrase "plane of the diaphragm" refers to the generally planar surface of the diaphragm (disc).

As used in the instant specification and claims, the phrase "suspended diaphragm" designates a diaphragm having at least a suspension member as described below. The diaphragm and suspension member are operatively associated with an immobilization means as described below. For example, the suspended diaphragm may be constructed according to the teachings of U.S. Pat. No. 4,440,258 to Packard (the entire contents of which are herein incorporated by reference).

Referring first to FIG. 1, a stethoscope 10 includes a chestpiece 12 formed of conventional material utilized in the fabrication of stethoscope heads, for example, metals such as stainless steel and aluminum, metallic composites, plastic and wood. The chestpiece 12 is attached to a conventional headset such as that described in U.S. Pat. No. 4,200,169 which includes an elongated flexible tubing 14 that splits into flexible tubings 16 that run to ear tips 18. The lower end of the flexible tubing 14 is adapted to be coupled to a conventional stem fitting on the chestpiece 12. The coupling may utilize the indexing detent as taught in U.S. Pat. No. 4,770,270 (the entire contents of which are herein expressly incorporated by reference). Binaural tubes for stethoscopes can be prepared in accordance with the teachings of U.S. Pat. Nos. 5,111,904; 5,380,182; and U.S. Pat. No. 5,324,471 to Packard et al. (each of which is hereby incorporated by reference).

Ear tips 18 are sized and shaped to engage the surfaces of the user's ears. The ear tips 18 may include any suitable ear tips. In one embodiment, the ear tips 18 include the soft ear tips disclosed in U.S. Pat. Nos. 4,852,684; 4,913,259 and 5,449,865 (the entire contents hereby incorporated by reference).

Referring to one embodiment shown in FIGS. 2-4, the chestpiece 12 is a dual-sided chestpiece including a first sound collecting side 20 and a second sound collecting side 22. It should be noted that although the one piece diaphragm of the present invention is discussed with respect to a dual-sided chestpiece, the one piece diaphragm may also be used with a single-sided chestpiece without limiting the scope of the present invention. In addition, while the figures depict a dual-sided chest piece, each with suspended (tunable) diaphragms, the one piece diaphragm of the present invention may be used with a non-suspended configuration (non-tunable). In one embodiment, the stethoscope 10 affords tuning in of sound while using either the first side 20 or the second side 22 of the chestpiece 12. The first sound collecting side 20 is sized and shaped to collect sounds from adult patients. The second sound collecting side 22 is substantially smaller than the first sound collecting side to afford easier access to remote or difficult to reach locations. Thus, the second sound collecting side 22 is sized and shaped to afford sufficient surface contact on pediatric or thin patients.

Figure 3B:
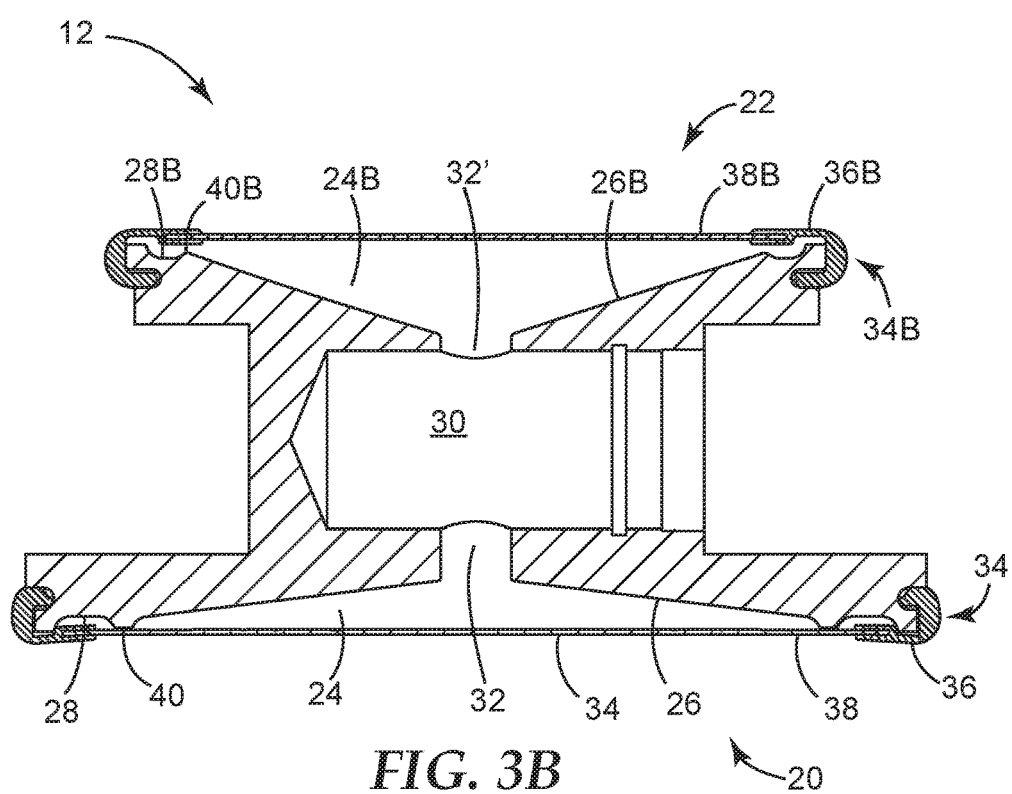
FIG. 3B is a cross-sectional view of an assembled chestpiece showing a diaphragm of the one piece diaphragms of the present invention in an inner position.

The first sound collecting side 20 has a first recess 24 with an innermost central portion 26, an outer rim portion 28, and an acoustic channel 30, 32 communicating with the central portion 26. A first diaphragm 34 is a suspended diaphragm and is also located on the first sound collecting side 20. The first diaphragm 34 includes a rim 36 and disc 38 positioned within the rim 36, together having a peripheral edge portion and a predetermined surface contour overlying at least a portion of the first recess 24. As shown in FIGS. 3A and 3B, the first diaphragm 34 is moveably connected to or "operatively associated" with the outer rim portion 28 of the first recess 24.

The first diaphragm 34 is positioned on the chestpiece 12 such that there can be movement of the first diaphragm 34 in a direction substantially perpendicular to the plane of the first diaphragm 34 between: 1) a normal outer position to which the first diaphragm 34 is biased and 2) an inner position more closely adjacent the central portion of the first recess 24. This movement is accomplished without substantially changing the surface contour of or the lateral tension in the first diaphragm 34.

A first immobilizing means 40 is situated on the first sound collecting side 20 of the chestpiece 12. The first immobilizing means 40 is located within the first recess 24. Together with the central portion of the first recess 24, the first immobilizing means 40 forms a shallow recess within the first recess 24. The immobilizing means 40 is sized and shaped to be contacted by the first diaphragm 34. In FIG. 3B, it is the first diaphragm 34 which contacts the immobilizing means 40. When the first diaphragm 34 is in the inner position, the immobilizing means 40 immobilizes the first diaphragm 34.

The first sound collecting side 20 of the chestpiece 12 will pass low frequency (bass) sounds and gradually attenuate sounds with higher frequencies when the first diaphragm 34 is in the outer position and between the outer and inner positions. When the first diaphragm 34 is in the inner position, the acoustical stiffness of the first diaphragm 34 will be significantly higher than the acoustical stiffness of the first diaphragm 34 when it is in the outer position, so that the first sound collecting side 20 of the chestpiece 12 will attenuate or block low frequency sounds while leaving higher frequency sounds unchanged. In use, a physician would simply modify the manual pressure exerted on the chestpiece 12 in order to switch between the outer and inner positions. In one embodiment, the level of bass attenuation varies from about 3 to about 21 dB.

The second sound collecting side 22 is adapted to include a second suspended diaphragm. The second sound collecting side 22 has many reference characters similar to the reference characters used to describe elements of the first sound collecting side 20 except that the reference character "B" has been added. The second sound collecting side 22 has a second recess 24B with an innermost central portion 26B, an outer rim portion 28B, and an acoustic channel 30, 32' communicating with the central portion 26B. The second sound collecting side 22 has a second diaphragm 34B including a rim 36B and disc 38B positioned within the rim 36B, together having with a peripheral edge portion and a predetermined surface contour overlying at least a portion of the second recess 24B. The second diaphragm 34B is moveably associated with the outer rim portion 28B of the second recess 24B.

A second immobilizing means 40B is situated on the second sound collecting side 22 of the chestpiece 12. The second immobilizing means 40B is located within the second recess 24B. Together with the central portion 26B of the second recess 24B, the second immobilizing means 40B forms a shallow recess within the second recess 24B. The second immobilizing means 40B is sized and shaped to be contacted by the second diaphragm 34B. When the second diaphragm 34B is in the inner position (not shown in FIGS.), the second immobilizing means 40B immobilizes the second diaphragm 34B.

The second sound collecting side 22 of the chestpiece 12 will pass low frequency sounds and gradually attenuate sounds with higher frequencies when the second diaphragm 34B is in the outer position and between the outer and inner positions. When the second diaphragm 34B is in the inner position, the acoustical stiffness of the second diaphragm 34B will be significantly higher than its first acoustical stiffness so that the second sound collecting side 22 of the chestpiece 12 will attenuate or block low frequency sounds while leaving higher frequency sounds unchanged. In one embodiment, the level of bass attenuation varies from about 3 to about 21 dB.

The size and shape of the first sound collecting side 20 is different than the size and shape of the second sound collecting side 22.

In one embodiment, the immobilizing means 40 and 40B include ridges machined into the metal of the chestpiece 12 (see FIGS. 3A and 3B). Other immobilizing means which are suitable for employment in the stethoscope heads of the present invention include O-rings, molded ridges, and inserts (e.g., plastic inserts). For example, the machined ridge 40B may have an inner diameter of about 1.053 inches, a depth radius of about 0.016 inches (0.41 millimeters), and a width of 0.015 inches (0.38 millimeters).

The diaphragms 34 and 34B overlay their respective recesses 24 and 24B sufficiently to afford contact of the diaphragms with the immobilizing means 40 and 40B. The rims 36 and 36B and discs 38 and 38B of diaphragms 34 and 34B may comprise any material which is known in the art as being suitable for use as a diaphragm. In one embodiment, the rim and the disc may be formed of different materials. In another embodiment, the rim and the disc may be formed of the same material. While in most cases it is preferred that the rim and the disc are formed of different materials due to the different requirements of the rim and the disc, the rim and the disc may be made of the same material. For example, in one embodiment when the rim and the disc are formed of different materials, the rim is formed of a polymeric resin while the disc is formed of plastic. In an embodiment when the rim and the disc are formed of the same material, the rim and the disc may be formed of a flexible material so that the one piece diaphragm can be put on the chestpiece. Examples of suitable materials when the rim and the disc are formed of one material include, but are not limited to: silicone, rubber, urethane, thermoplastic elastomers, flexible plastics such as polyphenylene ether, and fiberglass. A suitable thickness for the diaphragms 34 and 34B is about 5 to 20 mils (13 to 51 μm).

The response of chestpiece 12 to low frequency and high frequency sounds is affected by several parameters. The thickness of the diaphragm affects the response, and suitable thicknesses for the diaphragms have been discussed hereinabove. Also, the relative dimensions of first recess and second recess affect the response. The following have been found to be suitable dimensions for the recess 24B: the recess 24B has a diameter of about 1.32 inches (3.35 centimeters), a major radius as seen in FIGS. 3A and 3B of about 0.196 inches (4.98 millimeters), an initial major depth of about 0.22 inches (5.6 millimeters) and a secondary depth of about 0.235 inches (5.97 millimeters). The passage 32' has a diameter of about 0.125 inches (3.175 millimeters).

It is contemplated that the acoustical stiffness of the diaphragm can be increased suitably by contact of the suspension member with the immobilizing means.

Figure 4A:
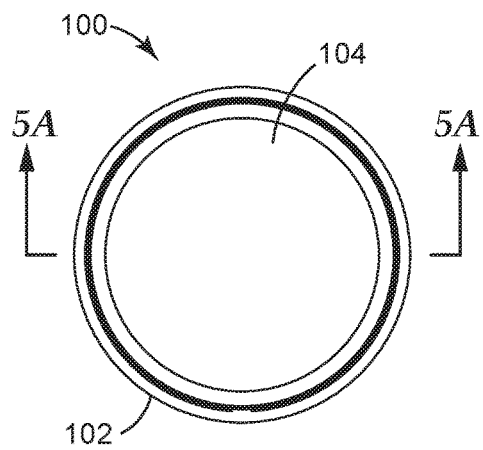
FIG. 4A is a top view of a first embodiment of an adult-sized one piece diaphragm of the present invention.
Figure 4B:
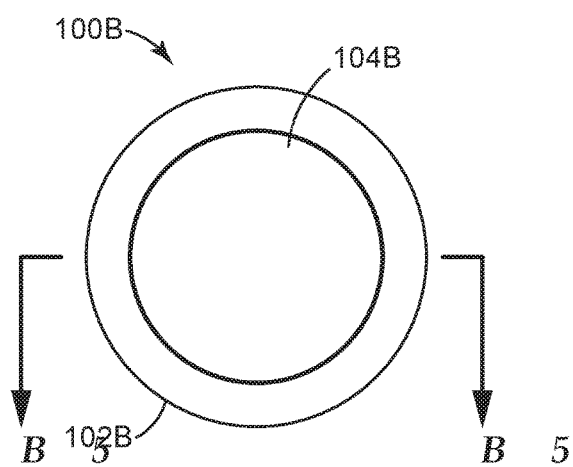
FIG. 4B is a top view of a first embodiment of a pediatric-sized one piece diaphragm of the present invention.
Figure 5A:
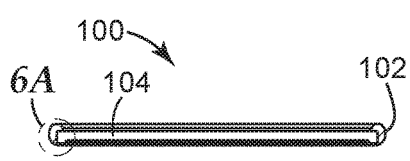
FIG. 5A is a cross-sectional view of the first embodiment of an adult-sized one piece diaphragm of the present invention along lines 5A-5A of FIG. 4A.
Figure 5B:
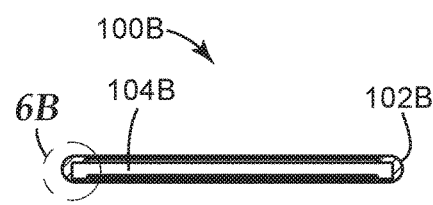
FIG. 5B is a cross-sectional view of the first embodiment of a pediatric-sized one piece diaphragm of the present invention along lines 5B-5B of FIG. 4B.
Figure 6A:
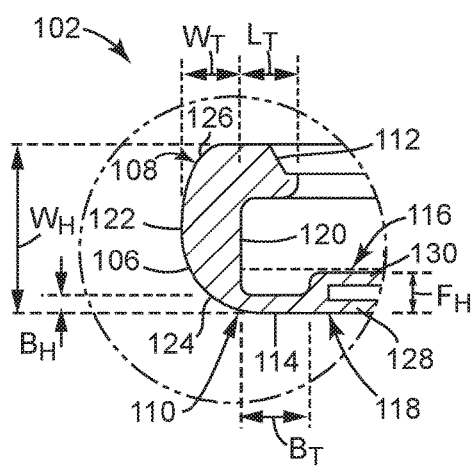
FIG. 6A is an enlarged view of a part of the first embodiment of the adult-sized one piece diagram of the present invention shown in FIGS. 4A and 5A.
Figure 6B:
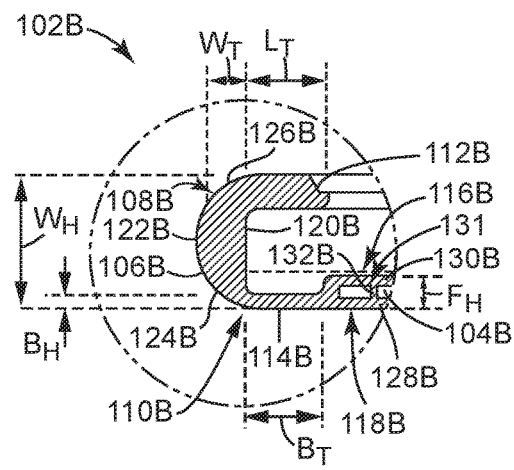
FIG. 6B is an enlarged view of a part of the first embodiment of the pediatric-sized one piece diagram of the present invention shown in FIGS. 4B and 5B.

Turning now to FIGS. 4A, 4B, 5A, 5B, 6A and 6B, a first embodiment of the one piece diaphragms of the present invention will be described in more detail. FIGS. 4A, 5A and 6A show an embodiment on an adult-sized one piece diaphragm 100 of the present invention and FIGS. 4B, 5B and 6B show an embodiment of a pediatric-sized one piece diaphragm 100B of the present invention. FIGS. 4A and 4B show top views of the adult and pediatric-sized one piece diagrams 100 and 100B, respectively, according to a first embodiment of the present invention. FIG. 5A shows the adult-sized diaphragm 100 at lines 5A-5A of FIG. 4A and FIG. 5B shows the pediatric-sized diaphragm 100B at lines 5B-5B of FIG. 4B. FIG. 6A shows an enlarged view of a section of the adult-sized diaphragm 100 of FIGS. 4A and 5A. FIG. 6B shows an enlarged view of a section of the pediatric-sized diaphragm 100B of FIGS. 4B and 5B. The pediatric-sized diaphragm 100B has many reference characters similar to the reference characters used to describe elements of the adult-sized diaphragm 100 except that the reference character "B" has been added. The elements otherwise function similarly. As mentioned above, the one piece diaphragm 100, 100B includes a rim 102, 102B and a disc 104, 104B. The rim 102, 102B and the disc 104, 104B may be made from different materials but are a unitary piece when fabricated. The rim 102, 102B includes a wall 106, 106B having a first end 108, 108B and a second end 110, 110B, a lip 112, 112B extending substantially perpendicularly from the first end 108, 108B of the wall 106, 106B, a bridge 114, 114B extending substantially perpendicularly from the second end 110, 110B of the wall 106, 106B, a chestpiece outer diameter contact surface 116, 116B and a fork 118, 118B extending from the bridge 114, 114B. In one embodiment, the rim is formed from one of a polymeric resin, silicone, rubber, flexible plastic and fiberglass.

The wall 106, 106B has a circular or ring-shaped configuration and functions to maintain the diaphragm 100, 100B on the chestpiece 12, 12B. The wall 106, 106B has an inner side 120, 120B and an opposite outer side 122, 122B, a patient facing edge 124, 124B and an opposite chestpiece facing edge 126, 126B. The wall 106, 106B must be thick enough to have sufficient rigidity to stay on the chestpiece 12, 12B. If the wall 106, 106B is too thick, the diaphragm 100, 100B may fall off of the chestpiece 12, 12B when a small amount of pressure is applied. For example, if the wall is too thick, when the chestpiece rubs on clothing, such as when a health care provider removes the chestpiece from a pocket, the diaphragm may unintentionally fall off of the chestpiece. In one embodiment, when the chestpiece 12 has a diameter of about 1.71 inches (43.43 millimeters) the adult-sized rim 102 has a wall thickness $W_T$ of between about 0.02 and about 0.10 inches (0.5 and 2.5 millimeters), particularly between about 0.03 and about 0.06 inches (0.76 and 1.54 millimeters) and more particularly between about 0.037 and about 0.043 inches (0.94 and 1.09 millimeters). In one embodiment, when the chestpiece 12B has a diameter of about 1.355 inches (34.42 millimeters) the pediatric-sized rim 102B has a wall thickness $W_T$ of between 0.02 and 0.1 inches (0.5 and 2.5 millimeters), particularly between 0.03 and about 0.06 inches (0.76 and 1.54 millimeters) and more particularly between about 0.037 and about 0.043 inches (0.94 and 1.09 millimeters). The height of the wall 106 is important in determining the height of the disc 104 above the chestpiece 12, which in turn affects tunability of the chestpiece 12. In one embodiment, the adult-sized rim 102 has a wall height $W_H$ of between about 0.084 and about 0.314 inches (2.13 and 7.98 millimeters), particularly between about 0.1 and about 0.25 inches (2.54 and 6.35 millimeters) and more particularly between about 0.111 and about 0.117 inches (2.82 and 2.97 millimeters). In one embodiment, the pediatric-sized rim 102B has a wall height $W_H$ of between about 0.08 and about 0.310 inches (2.03 and 7.87 millimeters), particularly between about 0.1 and about 0.25 inches (2.54 and 6.35 millimeters) and more particularly between about 0.107 and about 0.113 inches (2.72 and 2.87 millimeters).

The lip 112, 112B extends from the inner side 120, 120B at the first end 108, 108B of the wall 106, 106B at the chestpiece facing edge 124, 124B and functions to secure the diaphragm 100, 100B to the chestpiece 12, 12B. The chestpiece 12, 12B is inserted between the lip 112, 112B and the fork 118, 118B of the rim 102, 102B. The lip 112, 112B must hold the diaphragm 100, 100B tightly enough to stay on the chestpiece 12, 12B, but not so tight such that the diaphragm 100, 100B cannot be removed if desired, for example, for cleaning. In one embodiment, when the chestpiece 12 has a diameter of about 1.71 inches (43.43 millimeters), the adult-sized rim 102 has a lip thickness $L_T$ of between about 0.018 and about 0.188 inches (0.46 and 3 millimeters), particularly between about 0.025 and about 0.06 inches (0.64 and 1.52 millimeters) and more particularly between about 0.033 and about 0.039 inches (0.84 and 1 millimeter). In one embodiment, when the chestpiece 12B has a diameter of about 1.355 inches (34.42 millimeters), the pediatric-sized rim 102B has a lip thickness $L_T$ of between about 0.018 and about 0.118 inches (0.46 and 3 millimeters), particularly between about 0.025 and about 0.06 inches (0.64 and 1.52 millimeters) and more particularly between about 0.025 and about 0.031 inches (0.64 and 0.79 millimeters).

The bridge 114, 114B extends from the inner side 120, 120B of the second end 110, 110B of the wall 106, 106B at the patient facing edge 126, 126B. The bridge 114, 114B, and particularly the bridge height and thickness, allows the diaphragm 100, 100B to have sufficient flexibility to move and achieve good acoustics. The bridge height needs to be as thin as possible while minimizing the risk of the rim 102, 102B breaking during normal use. In one embodiment, when the chestpiece 12 has a diameter of about 1.71 inches (43.43 millimeters), the adult-sized rim 102 has a bridge height $B_H$ of between about 0.007 and about 0.028 inches (0.18 and 0.71 millimeters) (or substantially equal to the fork thickness), particularly between about 0.008 and about 0.02 inches (0.23 and 0.51 millimeters) and more particularly between about 0.009 and about 0.015 inches (0.23 and 0.38 millimeters). In one embodiment, when the chestpiece 12B has a diameter of about 1.355 inches (34.42 millimeters), the pediatric-sized rim 102B has a bridge height $B_H$ of between about 0.007 and about 0.028 inches (0.18 and 0.71 millimeters) (or substantially equal to the fork thickness), particularly between about 0.008 and about 0.02 inches (0.23 and 0.51 millimeters) and more particularly between about 0.009 and about 0.015 inches (0.23 and 0.38 millimeters). The bridge width should be as long as possible between the chestpiece outer diameter contact surface and the disc while still allowing filling during molding. In one embodiment, the adult-sized rim has a bridge thickness $B_T$ of between about 0.01 and about 0.5 inches (0.01 and 12.7 millimeters), particularly between about 0.025 and about 0.2 inches (0.64 and 5.08 millimeters) and more particularly between about 0.04 and about 0.048 inches (1.02 and 1.22 millimeters). In one embodiment, the pediatric-sized rim has a bridge thickness $B_T$ of between about 0.01 and about 0.5 inches (0.01 and 12.7 millimeters), particularly between about 0.25 and about 0.2 inches (0.64 and 5.08 millimeters) and more particularly between about 0.06 and about 0.066 inches (1.52 and 1.68 millimeters).

The chestpiece outer diameter contact surface 116, 116B functions to ensure a tight fit when the diaphragm 100, 100B is positioned on the chestpiece 12, 12B. The chestpiece outer diameter contact surface 116, 116B needs to be tight enough to create a good acoustic seal and so that the diaphragm 100, 100B does not rotate on the chestpiece 12, 12B and so that the diaphragm 100, 100B does not unintentionally come off of the chestpiece 12, 12B. In one embodiment, when the chestpiece 12 has a diameter of about 1.71 inches (43.43 millimeters), the adult-sized rim 102 has a chestpiece outer diameter (OD) contact surface 116 of between about 1.66 and 1.74 inches (4.22 and 4.42 centimeters), particularly between about 1.685 and about 1.720 inches (4.28 and 4.37 centimeters) and more particularly between about 1.693 and about 1.703 inches (4.3 and 4.33 centimeters). In one embodiment of the adult-sized rim 102, the diaphragm 100 has an interference of about 0.012 with the chestpiece outer diameter. In another embodiment of the adult-sized rim 102, the diaphragm 100 has an interference of up to about 0.05 with the chestpiece outer diameter or up to about 0.30 clearance. In one embodiment, when the chestpiece 12B has a diameter of about 1.335 inches (34.42 millimeters) the pediatric-sized rim 102B has a chestpiece outer diameter (OD) contact surface 116B of between about 1.296 and 1.376 inches (3.29 and 3.5 centimeters), particularly between about 1.225 and about 1.360 inches (3.11 and 3.45 centimeters) and more particularly between about 1.341 and about 1.351 inches (3.41 and 3.43 centimeters). In one embodiment of the pediatric-sized rim 102B, the diaphragm 100B has an interference of about 0.010 inches (0.25 millimeters) with the chestpiece outer diameter. In another embodiment of the pediatric-sized rim 102B, the diaphragm 100B has an interference of up to about 0.05 inches (1.27 millimeters) with the chestpiece outer diameter or up to about 0.30 inches (7.62 millimeters) clearance.

The fork 118, 118B extends from the bridge 114, 114B and functions to secure the disc 104. 104B within the rim 102, 102B and includes a first flange 128, 128B and a second flange 130, 130B substantially perpendicular to the first flange 128, 128B. The disc 104, 104B is positioned between the first and second flanges 128, 128B and 130, 130B, where it is maintained within the rim 102, 102B. The fork flanges 128, 128B and 130, 130B need to be just thick enough to allow filling on both sides of the disc 104, 104B during the molding process. In one embodiment, when the chestpiece 12 has a diameter of about 1.71 inches (43.43 millimeters), the adult-sized rim 102 has a fork height $F_H$ of between about 0.021 and about 0.057 inches (0.53 and 1.45 millimeters), particularly between about 0.022 and about 0.047 inches (0.56 and 1.19 millimeters) and more particularly between about 0.024 and about 0.03 inches (0.61 and 0.76 millimeters). In one embodiment, when the chestpiece 12B has a diameter of about 1.355 inches (34.42 millimeters), the pediatric-sized rim 102B has a fork height $F_H$ of between about 0.021 and about 0.057 inches (0.53 and 1.45 millimeters), particularly between about 0.022 and about 0.047 inches (0.56 and 1.19 millimeters) and more particularly between about 0.024 and about 0.03 inches (0.61 and 0.76 millimeters).

The disc 104, 104B may be formed of any material which is known in the art as being suitable for use as a diaphragm disc. Examples of suitable materials include plastics such as polyester, fiberglass-reinforced plastics, flexible plastics, silicone, rubber, fiberglass, polycarbonates, carbon fiber composites, polystyrene and metals such as stainless steel. A suitable thickness for the disc is about 5 to about 20 mils (13 to 51.mu.m) and particularly about 10 to about 12 mils (25 to 30.mu.m). In one embodiment, the disc is a 10 mil-thick (25.mu.m-thick) epoxy resin-fiberglass laminate. In one embodiment, the disc 104, 104B may include at least one aperture 131 along a periphery of the disc. In one embodiment, the disc includes a plurality of apertures 131 along the periphery of the disc. The apertures aid in maintaining the disc 104, 104B to the rim 102, 102B during molding and long term use of the diaphragm 100, 100B. In the unitary molding process, the disc 104, 104B is placed in the one piece diaphragm rim die tool (for example an injection mold). The material used for the rim 102, 102B is then melt molded (for example injection molded) around the edge of the diaphragm disc 104, 104B to form a unitary single piece diaphragm 100, 100B, which includes the rim 102, 102B. In one embodiment, the material flows through the one or more apertures 131 along the periphery of the disc to securely bond the rim portion to the disc portion of the unitary single piece diaphragm by forming a bond 132B (shown only in FIG. 6B) between the flanges 128B and 130B of the fork 118B. In one embodiment, the material used for the rim is a polymeric resin material.

Turning now to FIGS. 7A, 7B, 8A, 8B, 9A and 9B, another embodiment of the one piece diaphragms of the present invention will be described in more detail. FIGS. 7A, 8A and 9A show a second embodiment on an adult-sized one piece diaphragm 200 of the present invention and FIGS. 7B, 8B and 9B show a second embodiment of a pediatric-sized one piece diaphragm 200B of the present invention. FIGS. 7A and 7B show top views of the adult and pediatric-sized one piece diagrams 200 and 200B, respectively, according to the second embodiment of the present invention. FIG. 8A shows an adult-sized diaphragm 200 at lines 8A-8A of FIG. 7A and FIG. 8B shows a pediatric-sized diaphragm 200B at lines 8B-8B of FIG. 7B. FIG. 9A shows an enlarged view of a section of the adult-sized diaphragm 200 of FIGS. 7A and 8A. FIG. 9B shows an enlarged view of a section of the pediatric-sized diaphragm 200B of FIGS. 7B and 8B. Similar to the first embodiment, the pediatric-sized diaphragm 200B has many reference characters similar to the reference characters used to describe elements of the adult-sized diaphragm 200 except that the reference character "B" has been added. The elements otherwise function similarly. The second embodiment of the diaphragm 200 and 200A is very similar to the first embodiment of the diaphragm 100 and 100A. The diaphragm 200, 200B includes a rim 202, 202B and a disc 204, 204B that are a unitary piece when assembled. The rim 202, 202B includes a wall 206, 206B having a first end 208, 208B and a second end 210, 210B, a lip 212, 212B extending substantially perpendicularly from the first end 208, 208B of the rim 202, 202B, a bridge 214, 214B extending substantially perpendicularly from the second end 210, 210B of the rim 202, 202B, chestpiece outer diameter contact surface 216, 216B, and a fork 218, 218B extending from the bridge 214, 214B and over both sides of the disc 204, 204B. The only difference between the first and second embodiments of the diaphragm is that the second embodiment 200, 200B includes a step 232, 232B between the wall 206, 206B and the bridge 214, 214B.

The step 232, 232B functions to maintain the disc 204, 204B at a desired distance from the chestpiece 12, 12B and to maintain the diaphragm 200, 200B to the chestpiece 12, 12B. The step 232, 232B is positioned at the intersection of the second end 210, 210B of the wall 206, 206B and the bridge 214, 214B. In one embodiment, the step 232, 232B has a height substantially equal to the height of the fork 218, 218B. The thickness of the step 232, 232B can be up to the thickness of the bridge 214, 214B. In one embodiment, when the chestpiece 12 has a diameter of about 1.71 inches (43.43 millimeters), the adult-sized rim 202 has a step thickness ST of up to about 0.048 inches (i.e., all the way to the fork 218) (1.22 millimeters), particularly up to about 0.028 inches (0.71 millimeters) and particularly up to about 0.007 inches (0.18 millimeters) or eliminated completely. In one embodiment, when the chestpiece 12B has a diameter of about 1.355 inches (34.29 millimeters), the pediatric-sized rim 202B has a step thickness ST of up to about 0.066 inches (1.68 millimeters) (i.e., all the way to the fork 218B), particularly up to about 0.04 inches (1.02 millimeters) and more particularly up to about 0.007 inches (0.18 millimeters) or eliminated completely.

In practice, the disc is positioned within the fork of the rim. The fork and the rim are then made into a unitary piece, for example, by molding. In one embodiment, when the fork and the rim are integrally molded, portions of the fork are melted through any apertures in the disc, providing secure placement of disc within the rim. Upon assembly onto the chestpiece, the diaphragm must have enough flexibility to allow the diaphragm to be easily positioned on, and removed from, the chestpiece and rigid enough to ensure that the diaphragm does not unintentionally fall off of the chestpiece. In one embodiment, the rim has a Shore A durometer hardness of between about 40 and about 110, particularly between about 70 and about 90 and more particularly between about 75 and 85.

In another embodiment, the one piece diaphragm is made by providing an injection mold, providing a circular disc formed from a first material, positioning the disc within the injection mold, providing a second material, heating the second material, melt molding the second material into the injection mold and around a peripheral edge of the disc to form a one piece diaphragm and removing the one piece diaphragm from the injection mold. In one embodiment, the second material is a polymeric resin and the first material is plastic. In another embodiment, the first and the second material are the same, and may be, for example: silicone, rubber, flexible plastic or fiberglass.

The one piece diaphragm of the present invention offers numerous manufacturing benefits. The one piece diaphragm yields a diaphragm that is ready to be positioned on a chestpiece without the need for any secondary operations after molding. The one piece diaphragm design also allows the mold to run automatically, rather than manually, as is required on the two molds used today. Automation of the ejection step also allows for downstream automation, such as pad printing. All of the above benefits allows for reduced assembly costs. Because the one piece diaphragm can be easily produced at low cost, the diaphragms can be disposable or custom made.

Examples

The present invention is more particularly described in the following examples that are intended as illustrations only, since numerous modifications and variations within the scope of the present invention will be apparent to those skilled in the art. Unless otherwise noted, all parts, percentages, and ratios reported in the following example are on a weight basis.

Comparative Example 1 (C-EX.1) was a 3M LITTMANN CARDIOLOGY III Stethoscope (available from 3M Company of St. Paul, Minn.) used with the adult-sized (side) two piece diaphragm-rim assembly, as currently available from the manufacturer. The two piece rim components were comprised of a thermoplastic polyurethane and the diaphragm disc material was a 10 mil-thick (254 μm-thick) epoxy resin-fiberglass laminate. The chestpiece had a diameter of about 1.7 inches (43 millimeters).

Comparative Example 2 (C-EX.2) was a 3M LITTMANN CARDIOLOGY III Stethoscope (available from 3M Company of St. Paul, Minn.) used with the pediatric-sized (side) two piece diaphragm-rim assembly, as currently available from the manufacturer. The rim and diaphragm disc were made of the same materials as describe in Comparative Example 1. The chestpiece had a diameter of about 1.335 inches (34.42 millimeters) the pediatric-sized rim.

Example 1 (EX.1) was the same as C-EX.1, except the two piece diaphragm-rim assembly was replaced with the single-piece diaphragm assembly represented in FIGS. 4A, 5A, and 6A, sized to fit the adult side of the 3M LITTMANN CARDIOLOGY III Stethoscope, wherein the one piece rim material was injection molded around the diaphragm disc.

Example 2 (EX.2) was the same as C-EX.1, except the two piece diaphragm-rim assembly was replaced with the single-piece diaphragm assembly represented in FIGS. 7A, 8A, and 9A, sized to fit the adult side of the 3M LITTMANN CARDIOLOGY III Stethoscope, wherein the one piece rim material was injection molded around the diaphragm disc.

Example 3 (EX.3) was the same as C-EX.2, except the two piece diaphragm-rim assembly was replaced with the single-piece diaphragm assembly represented in FIGS. 4B, 5B, and 6B, sized to fit the pediatric side of the 3M LITTMANN CARDIOLOGY III Stethoscope, wherein the one piece rim material was injection molded around the diaphragm disc.

Example 4 (EX.4) was the same as C-EX.2, except the two piece diaphragm-rim assembly was replaced with the single-piece diaphragm assembly represented in FIGS. 7B, 8B, and 9B, sized to fit the pediatric side of the 3M LITTMANN CARDIOLOGY III Stethoscope, wherein the one piece rim material was injection molded around the diaphragm disc.

Example 5 (EX.5) was the same as EX.1, except the single-piece diaphragm assembly was attached to a 3M LITTMANN CLASSIC II SE Stethoscope.

Example 6 (EX.6) was the same as EX.1, except the single-piece diaphragm assembly was formed by injection molding thermoplastic polyurethane around a diaphragm disc also made of the same thermoplastic polyurethane. The diaphragm assembly of EX.6 was attached to a 3M LITTMANN CLASSIC II SE Stethoscope.

Stethoscope Acoustic Testing Apparatus and Procedure

Figure 10:
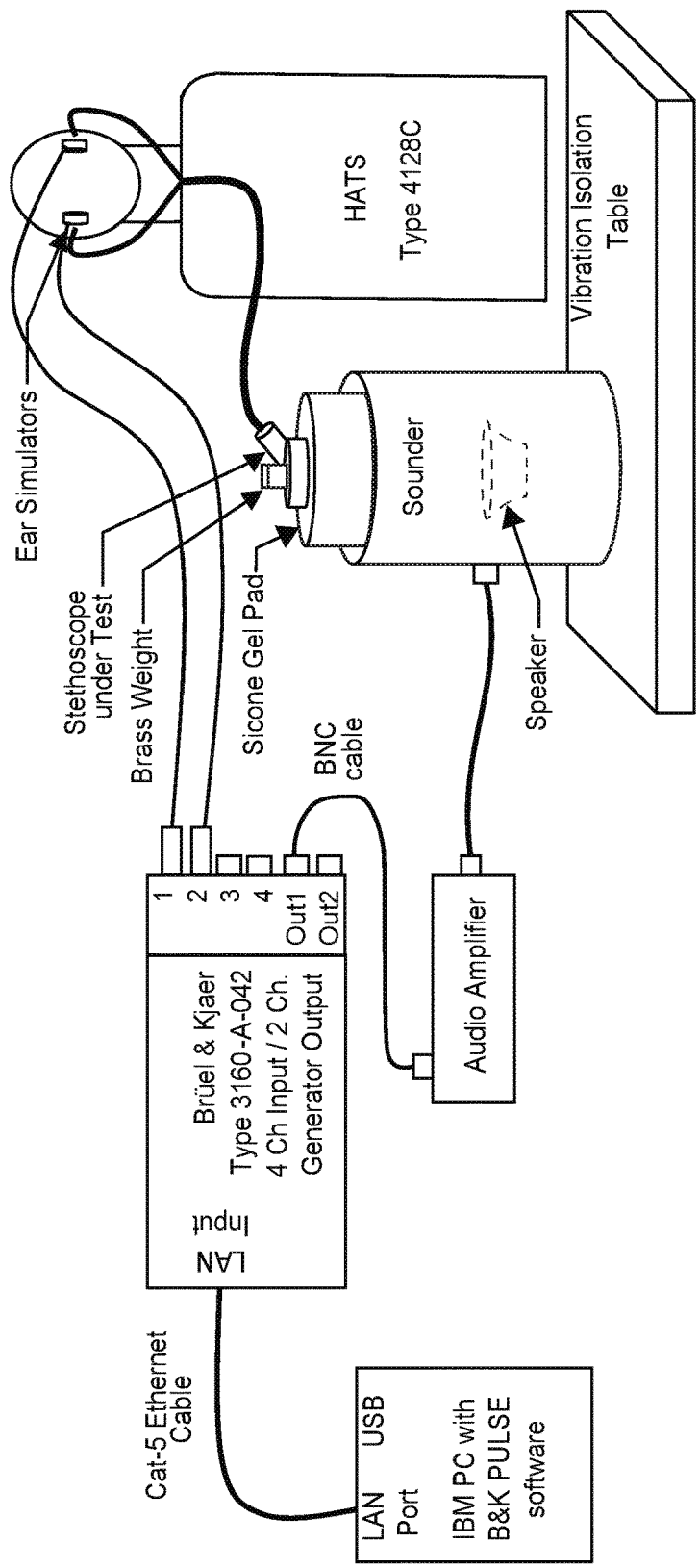
FIG. 10 is a diagram of a laboratory test set-up to generate an autospectrum frequency response of stethoscopes using the one piece diaphragms of the present invention.

Acoustic performance of a stethoscope can be described in terms of its frequency response to a broadband or pink noise source coupled to the chestpiece in a manner that simulates the human torso. The test apparatus used to characterize the acoustic performance of the Comparative Examples: C-EX.1 and C-EX.2, and the Examples EX.1-EX.4, is illustrated in FIG. 10. The equipment included: a Brüel & Kjær Head and Torso Simulator (HATS) type 4128C with 4159C Left Ear Simulator, 4158C Right Ear Simulator, and Calibrated Left and Right pinnae. The sound source was a loudspeaker enclosed in a cylindrical sounder chamber with an 87 millimeters opening on top filled by a silicone gel pad with dimensions of 130 millimeters diameter×30 millimeters thick. The silicone gel pad was used to simulate human skin/flesh and was made from ECOLFEX 00-10 Super Soft Shore 00-10 Platinum Silicone Rubber Compound, available from Reynolds Advanced Materials of Countryside, Ill., USA. A 3M LITTMANN CARDIOLOGY III Stethoscope (available from 3M Company of St. Paul, Minn.) was used with each of the example diaphragm assemblies tested. The stethoscope chestpiece with the attached example diaphragm assembly was placed on the gel pad. A select weight was applied to the top of the chest piece. The applied weight represented light (100 grams), medium (600 grams) or firm (1 kilogram or 1.2 kilogram) force that would be applied by a stethoscope user (clinician) to induce the tunable feature of the diaphragm of the CARDIOLOGY III Stethoscope. The stethoscope ear tips were inserted into the ears of a Head simulator. Microphones in the ear couplers detected the stethoscope sound as in a manner equivalent to the human ear.

Figure 11:
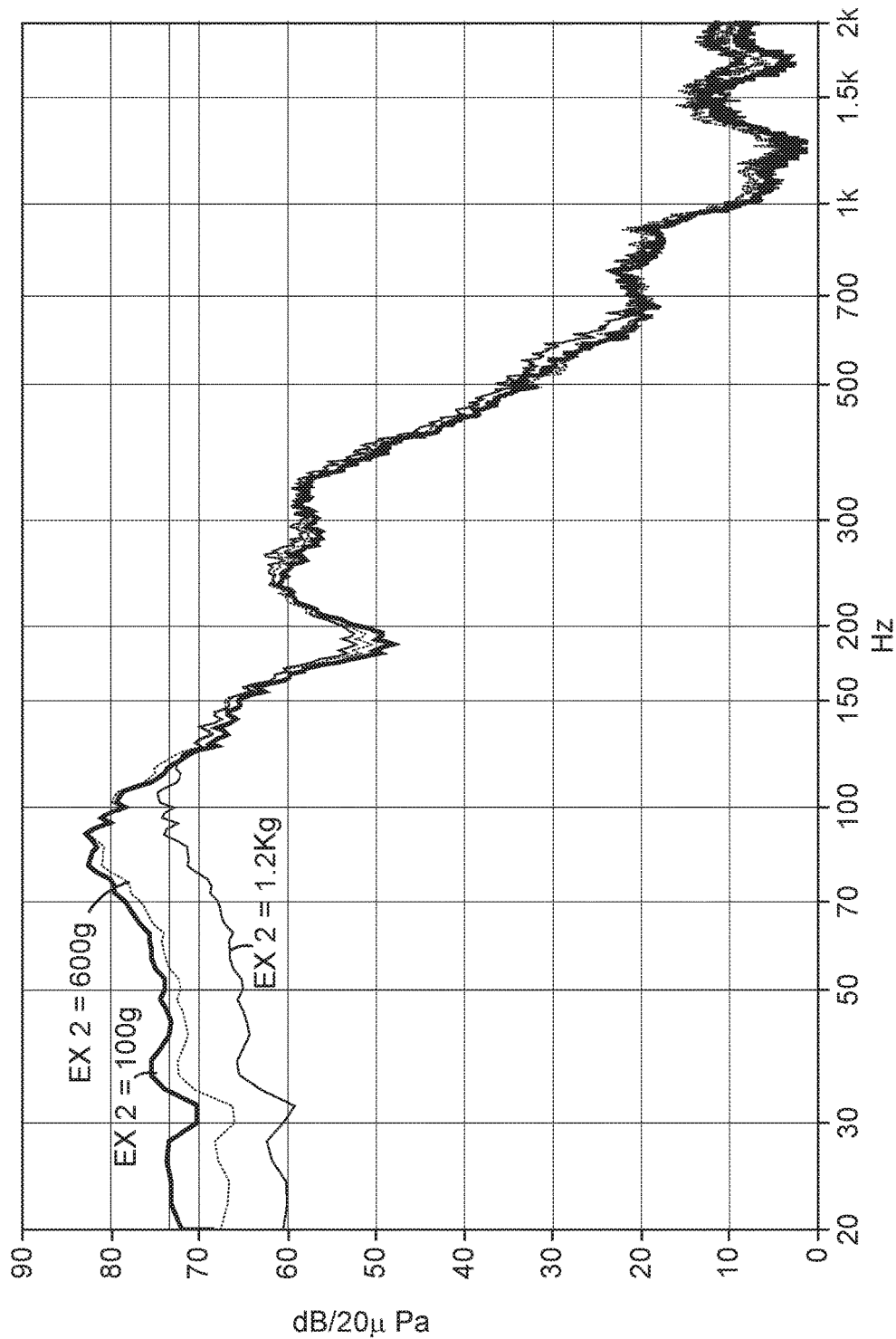
FIG. 11 is a graph showing the autospectrum frequency response curves for EX.2 with a 100 gram, 600 gram, and 1.2 kilogram weights, respectively.
Figure 12:
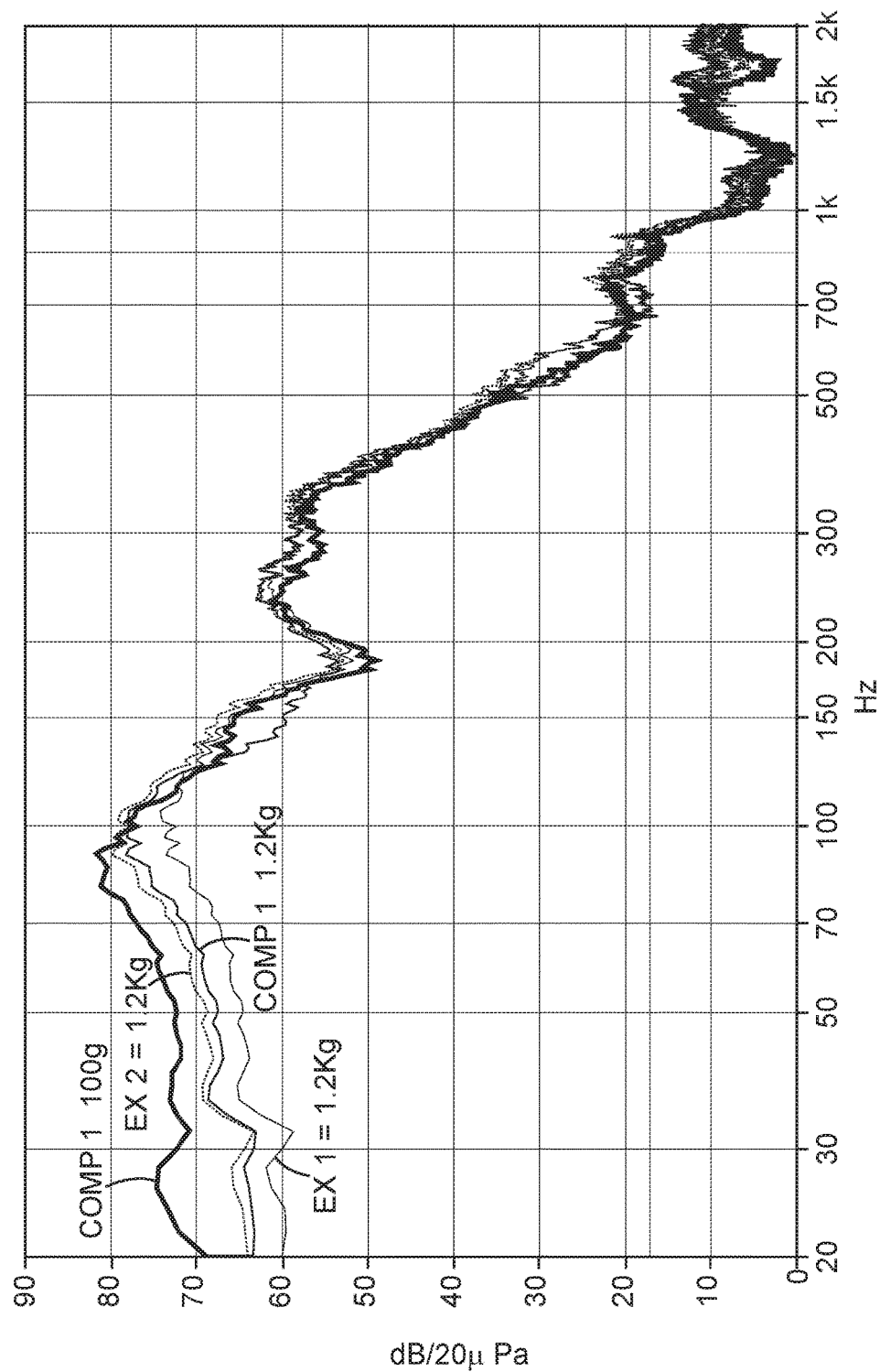
FIG. 12 is a graph showing the autospectrum frequency response curves for C-EX.1 with a 100 gram weight, EX.2 with a 1.2 kilogram weight, C-EX.1 with a 1.2 kilogram weight, and EX.1 with a 1.2 kilogram weight.
Figure 13:
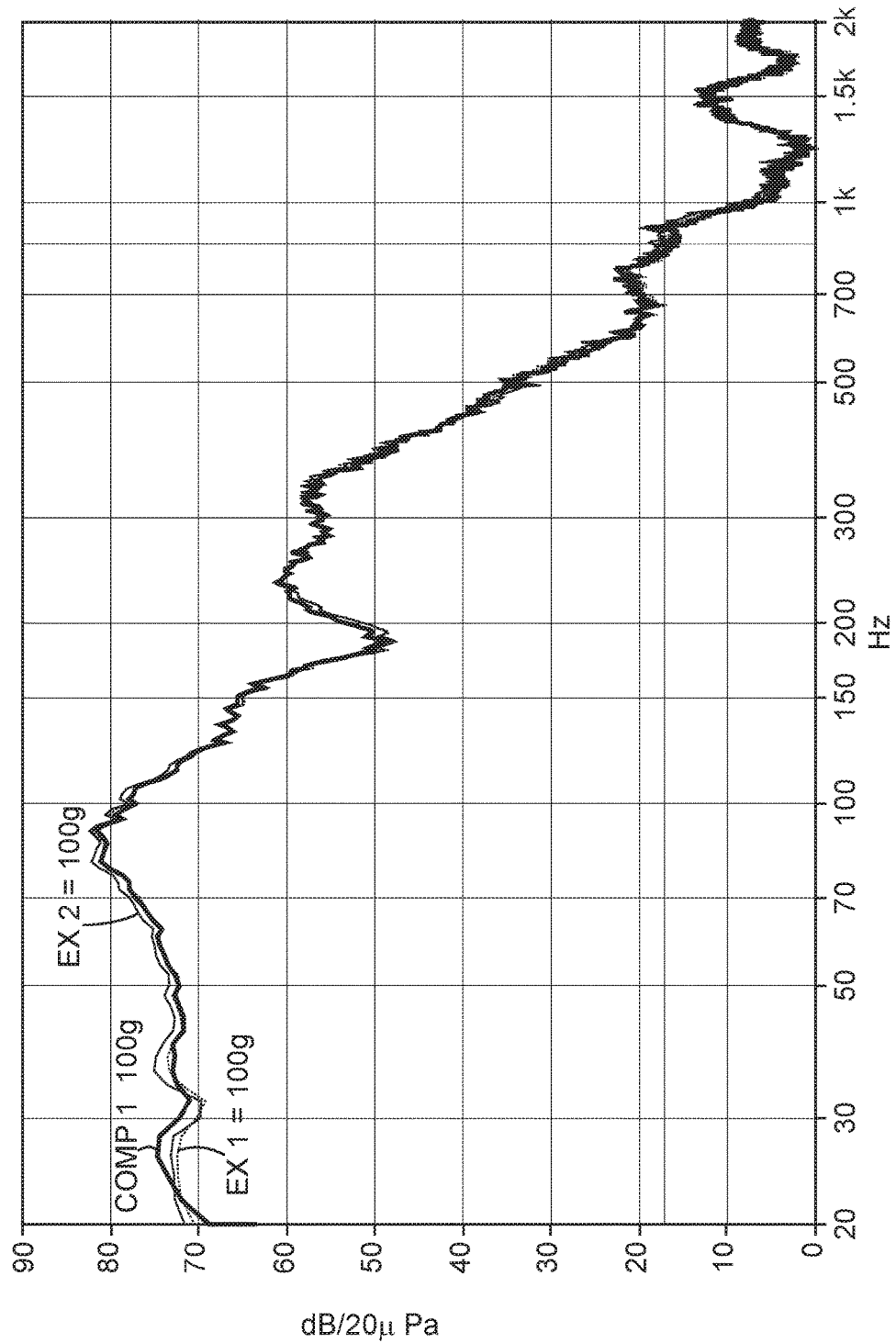
FIG. 13 is a graph showing the autospectrum frequency response curves for C-EX.1 with a 100 gram weight, EX.1 with a 100 gram weight, and EX.2 with a 100 gram weight.
Figure 14:
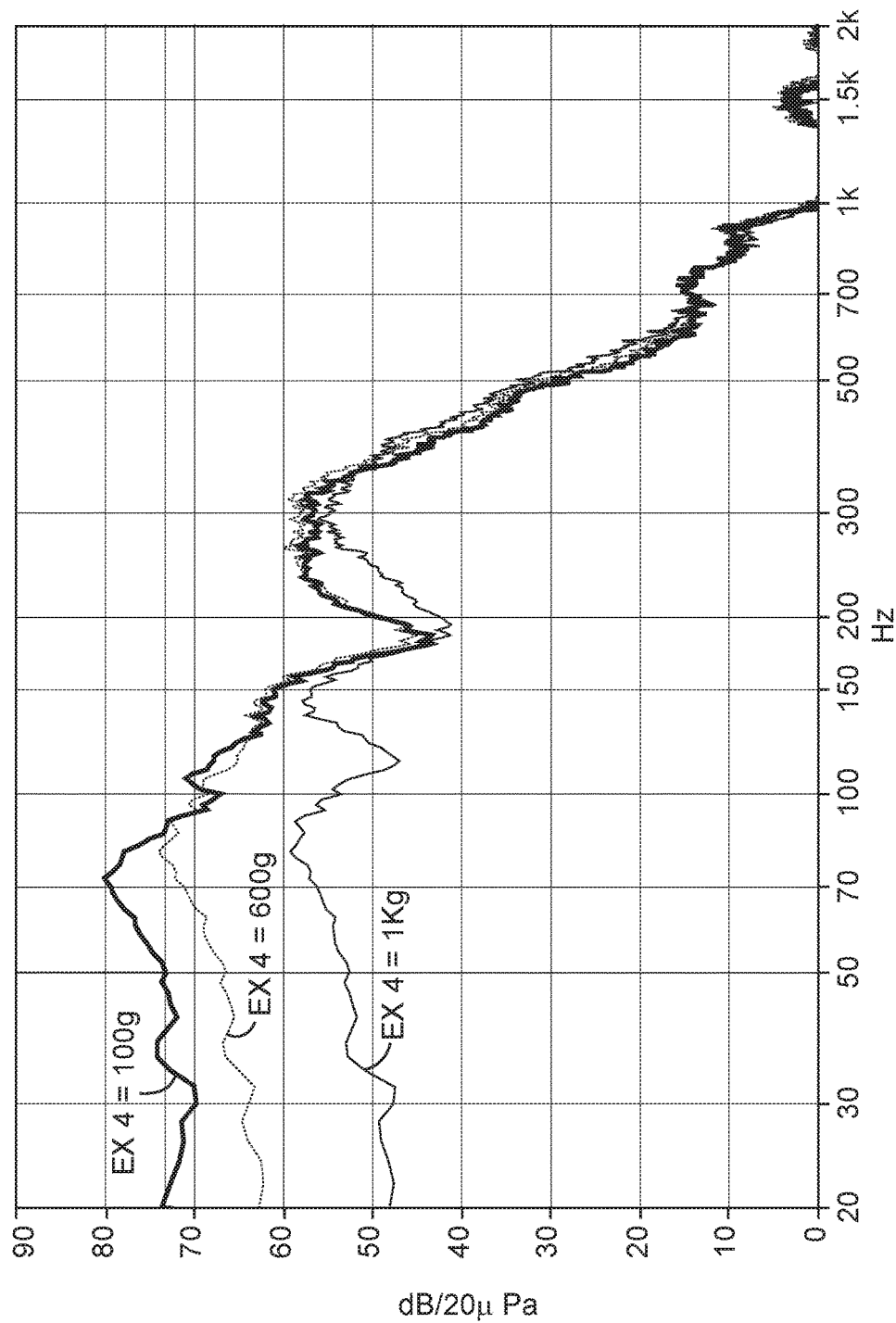
FIG. 14 is a graph showing the autospectrum frequency response curves for EX.4 with a 100 gram, 600 gram, and 1 kilogram weights, respectively.
Figure 15:
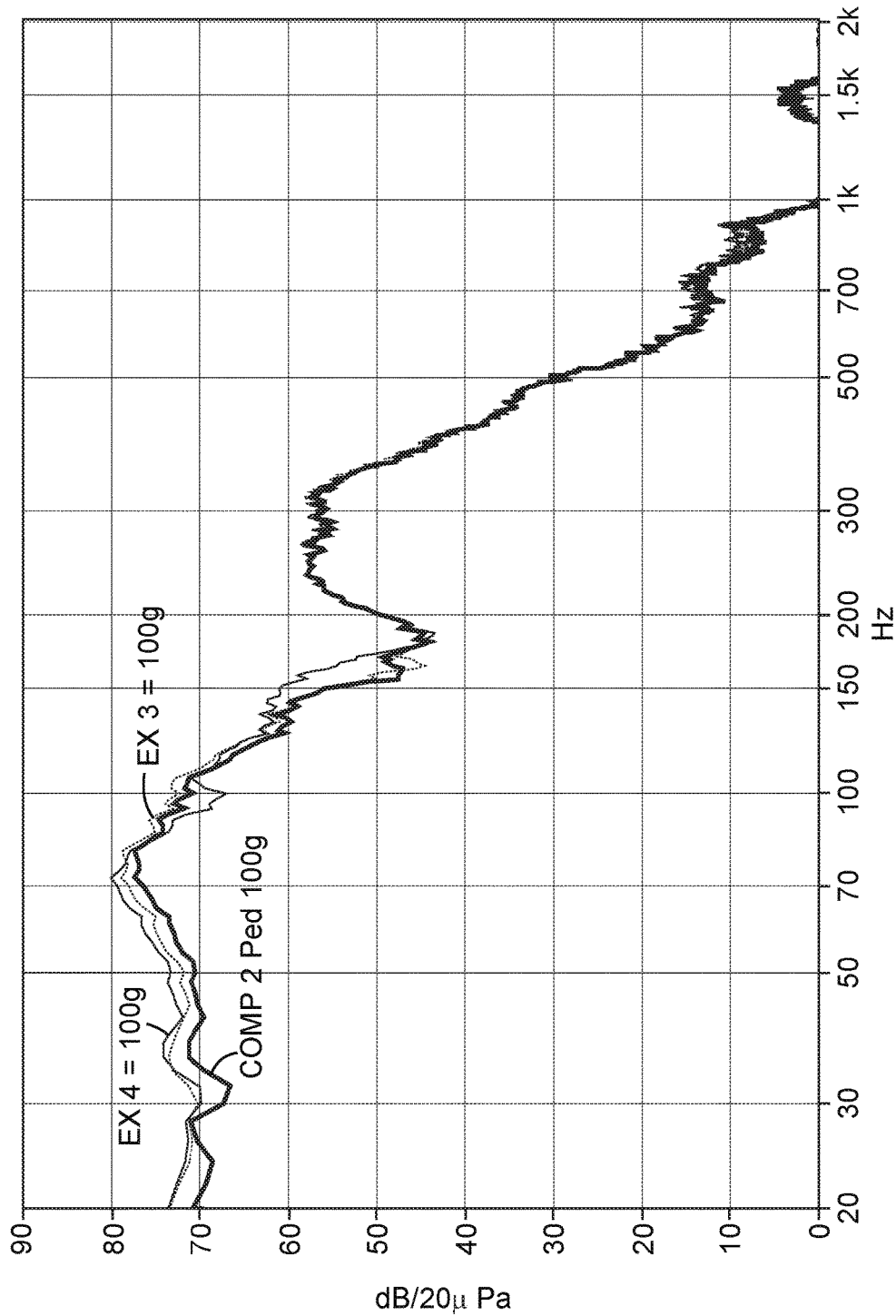
FIG. 15 is a graph showing the autospectrum frequency response curves for C-EX.2 with a 100 gram weight, EX.3 with a 100 gram weight, and EX.4 with a 100 gram weight.
Figure 16:
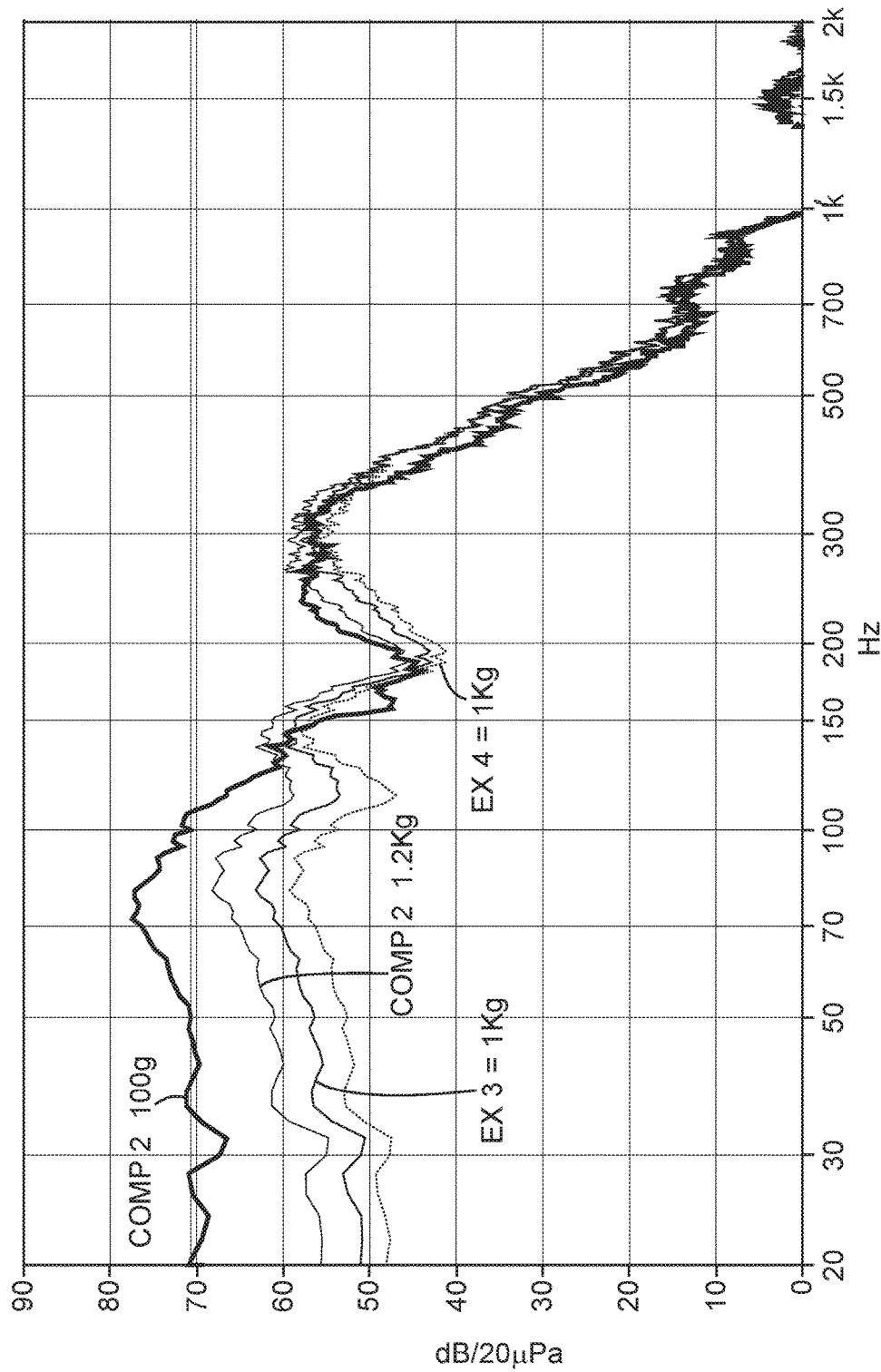
FIG. 16 is a graph showing the autospectrum frequency response curves for C-EX.2 with a 100 gram weight, C-EX.2 with a 1.2 kilogram weight, EX.3 with a 1 kilogram weight, and EX.4 with a 1 kilogram weight.

Sounds were generated, recorded and characterized by a Brüel & Kjaer (B&K) LAN-XI acoustic test system which operates with a PC using B&K PULSE software. An audio amplifier was used to drive the loudspeaker with sound produced by the LAN-XI system. The sounder cylinder with speaker inside was positioned on a 600 millimeter×900 millimeter Newport IsoStation Vibration Isolation Workstation. An autospectrum frequency response curve was generated for each Example with various weights used to apply a force to the chestpiece resting on the gel pad. Results for the adult-sized diaphragms are shown in FIGS. 11-13. Results for the pediatric-sized diaphragms are shown in FIGS. 14-16.

Figure 17:
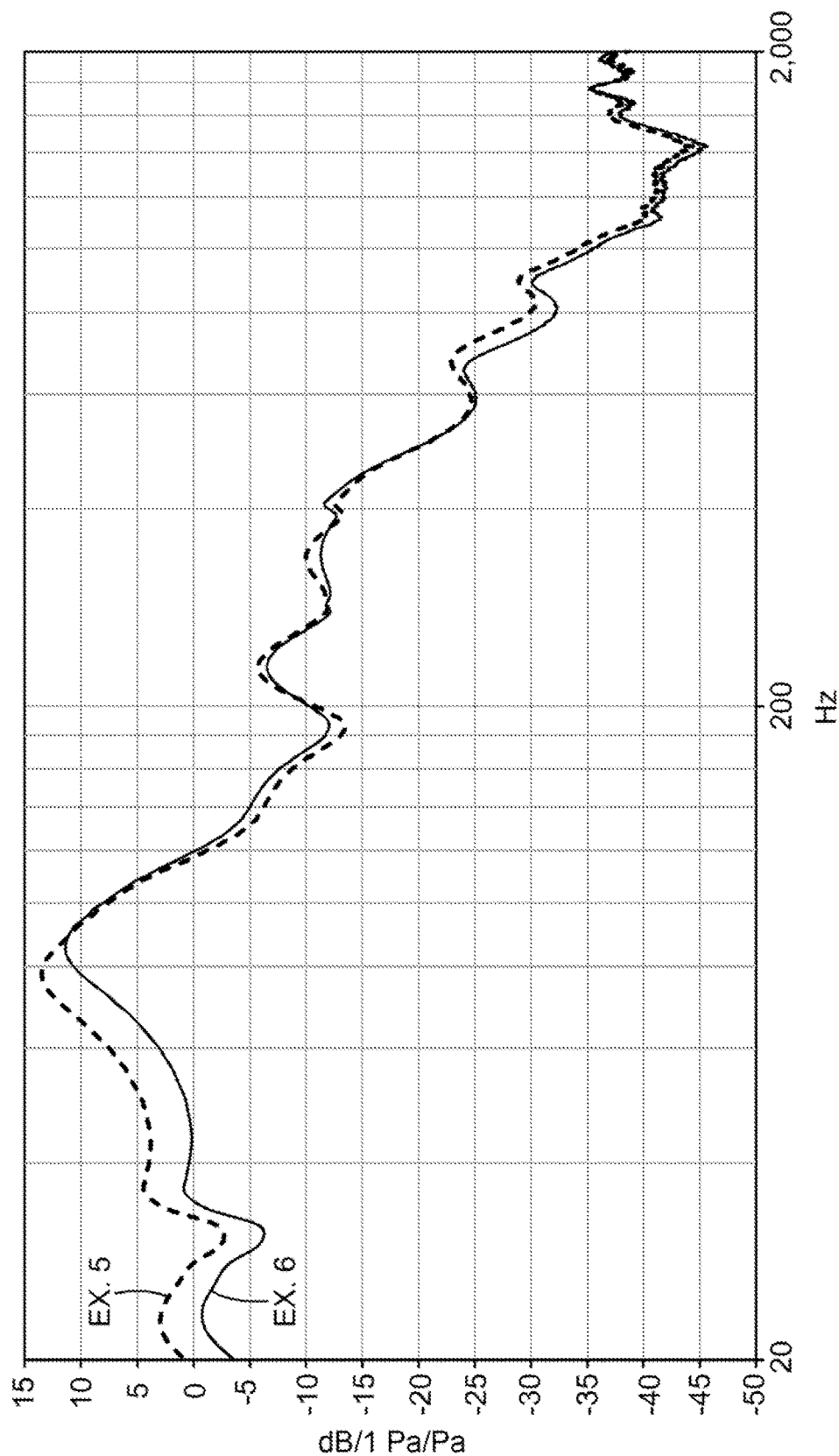
FIG. 17 is a graph showing the transfer function frequency response curves for Examples EX.5 vs. EX.6.

For Examples 5 and 6, a transfer function frequency response curve was generated for each example with a 100 gram weight used to apply a force to the chest-piece resting on the gel pad. Results are shown in FIG. 17.

FIG. 11 shows the autospectrum frequency response curves for EX.2 with a 100 gram, 600 gram, and 1.2 kilogram weights, respectively.

FIG. 12 shows the autospectrum frequency response curves for C-EX.1 with a 100 gram weight, EX.2 with a 1.2 kilogram weight, C-EX.1 with a 1.2 kilogram weight, and EX.1 with a 1.2 kilogram weight.

FIG. 13 shows the autospectrum frequency response curves for C-EX.1 with a 100 gram weight, EX.1 with a 100 gram weight, and EX.2 with a 100 gram weight.

FIG. 14 shows the autospectrum frequency response curves for EX.4 with a 100 gram, 600 gram, and 1 kilogram weights, respectively.

FIG. 15 shows the autospectrum frequency response curves for C-EX.2 with a 100 gram weight, EX.3 with a 100 gram weight, and EX.4 with a 100 gram weight.

FIG. 16 shows the autospectrum frequency response curves for C-EX.2 with a 100 gram weight, C-EX.2 with a 1.2 kilogram weight, EX.3 with a 1 kilogram weight, and EX.4 with a 1 kilogram weight.

FIG. 17 shows the transfer function frequency response curves for Examples EX.5 vs. EX.6, which compares the single-piece diaphragm assembly when it is made of two different materials for the disc and the rim (EX.5) and the single-piece diaphragm assembly when it is made of the same material for the disc and the rim (EX.6).

Although the present invention has been described with reference to preferred embodiments, workers skilled in the art will recognize that changes may be made in form and detail without departing from the spirit and scope of the invention.

What is claimed is:

1. A diaphragm comprising:
   a disc formed from a first material; and
   a rim formed from a second material, further comprising:
      a wall having a first end and a second end,
      a lip extending substantially perpendicularly from the first end of the wall,
      a bridge extending substantially perpendicularly from the second end of the wall, and
      a fork extending from the bridge;
   wherein the disc further comprises a plurality of apertures positioned around the periphery of the disc,
   wherein the second material forms a molded bond through the plurality of apertures,
   wherein the disc and the rim are a unitary piece, and
   wherein the rim has a Shore A durometer hardness of between about 40 and 110.

2. The diaphragm of claim 1, wherein the rim has a Shore A durometer hardness of between about 70 and 90.

3. The diaphragm of claim 1, wherein the first material and the second material are the same.

4. The diaphragm of claim 1, wherein the wall has a circular or a ring-shaped configuration, the wall having an inner side and an opposite outer side, and a patient facing edge and an opposite chestpiece facing edge;
   wherein the lip extends substantially perpendicularly from the inner side of the wall at the chestpiece facing edge; and
   wherein the bridge extends substantially perpendicularly from the inner side of the wall at the patient facing edge of the wall.

5. The diaphragm of claim 1, wherein the rim further comprises a step.

6. The diaphragm of claim 1, wherein the rim further comprises a plurality of bonds which fill the apertures and wherein the plurality of bonds each connect a first flange of the fork with a second flange of the fork.

7. A stethoscope comprising:
   a chestpiece; and
   a first one piece diaphragm positionable on the chestpiece, the first one piece diaphragm comprising:
      a disc made of a first material; and
      a rim made of a second material, further comprising:
         a wall having a first end and a second end,
         a lip extending substantially perpendicularly from the first end of the wall,
         a bridge extending substantially perpendicularly from the second end of the wall, and
         a fork extending from the bridge,
      wherein the disc further comprises a plurality of apertures positioned around the periphery of the disc,
      wherein the second material forms a molded bond through the plurality of apertures,
      wherein the rim has a Shore A durometer hardness of between about 40 and 110; and
      wherein the disc and the rim are a unitary piece.

8. The stethoscope of claim 7, wherein when the first one piece diaphragm is positioned on the chestpiece, the first one piece diaphragm is positionable between an inner position and an outer position such that when the first one piece diaphragm is in the outer position, the chestpiece will pass low frequency sounds and gradually attenuate higher frequency sounds and when the first one piece diaphragm is in the inner position, the chestpiece will attenuate low frequency sounds while leaving higher frequency sounds unaffected.

9. The stethoscope of claim 7, further comprising a second one piece diaphragm positionable on the chestpiece, the second one piece diaphragm comprising:
   a disc; and
   a rim,
   wherein the rim has a Shore A durometer hardness of between about 40 and 110; and
   wherein the disc and the rim are a unitary piece.

10. The stethoscope of claim 7, wherein the rim further comprises a step.

11. The stethoscope of claim 7, wherein the rim has a Shore A durometer hardness of between about 70 and 90.

12. The stethoscope according to claim 7, wherein the rim further comprises a plurality of bonds which fill the apertures and wherein the bonds each connect a first flange of the fork with a second flange of the fork.

13. The stethoscope of claim 6, wherein a patient facing surface of the rim of the one piece diaphragm is flat.

* * * * *

UNITED STATES PATENT AND TRADEMARK OFFICE
CERTIFICATE OF CORRECTION

Page 1 of 1

PATENT NO. : 10,398,406 B2
APPLICATION NO. : 15/500128
DATED : September 3, 2019
INVENTOR(S) : Joseph Keller et al.

It is certified that error appears in the above-identified patent and that said Letters Patent is hereby corrected as shown below:

In the Drawings

<u>Sheet 5 of 12, (FIG. 10)</u>
Line 4 (approx.)      Delete "Sicone" and insert -- Silicone --, therefor.

In the Specification

<u>Column 12</u>
Line 26      Delete "ECOLFEX" and insert -- ECOFLEX --, therefor.

In the Claims

<u>Column 14, (Claim 13)</u>
Line 55      Delete "stethoscope" and insert -- diaphragm --, therefor.

Signed and Sealed this
Twenty-fifth Day of August, 2020

Andrei Iancu
*Director of the United States Patent and Trademark Office*